United States Patent
Peterson et al.

(10) Patent No.: US 8,249,687 B2
(45) Date of Patent: Aug. 21, 2012

(54) SYSTEMS AND METHODS FOR VIRTUAL IDENTIFICATION OF POLYPS

(75) Inventors: Samuel W. Peterson, St. Paul, MN (US); Thomas J. Gleeson, Moss Beach, CA (US); Marek Brejl, Eden Praire, MN (US); Marguerite Kirkby, Minneapolis, MN (US)

(73) Assignee: Vital Images, Inc., Minnetonka, MN (US)

( * ) Notice: Subject to any disclaimer, the term of this patent is extended or adjusted under 35 U.S.C. 154(b) by 1598 days.

(21) Appl. No.: 11/198,929

(22) Filed: Aug. 5, 2005

(65) Prior Publication Data
US 2006/0276708 A1   Dec. 7, 2006

Related U.S. Application Data

(60) Provisional application No. 60/687,638, filed on Jun. 2, 2005.

(51) Int. Cl.
*A61B 5/05* (2006.01)
(52) U.S. Cl. .......... 600/407; 600/416; 600/431; 348/65; 382/128
(58) Field of Classification Search ............... 600/416, 600/431; 348/65; 382/128
See application file for complete search history.

(56) References Cited

U.S. PATENT DOCUMENTS

| 5,398,685 | A  | * | 3/1995  | Wilk et al. ................... 600/437 |
|-----------|----|---|---------|----------------------------------------|
| 7,574,029 | B2 |   | 8/2009  | Peterson et al.                        |
| 7,590,272 | B2 |   | 9/2009  | Brejl et al.                           |
| 2001/0031920 | A1 | * | 10/2001 | Kaufman et al. ............. 600/431 |
| 2002/0097320 | A1 | * | 7/2002  | Zalis .............................. 348/65 |
| 2003/0007673 | A1 | * | 1/2003  | Truyen et al. ................ 382/128 |
| 2003/0023163 | A1 | * | 1/2003  | Johnson et al. .............. 600/431 |
| 2003/0223627 | A1 | * | 12/2003 | Yoshida et al. .............. 382/128 |
| 2004/0267102 | A1 | * | 12/2004 | Skladnev et al. ............ 600/315 |
| 2005/0054895 | A1 | * | 3/2005  | Hoeg et al. ................... 600/117 |
| 2005/0078858 | A1 | * | 4/2005  | Yao et al. ..................... 382/128 |
| 2005/0107695 | A1 | * | 5/2005  | Kiraly et al. ................. 600/431 |
| 2005/0163356 | A1 | * | 7/2005  | Makram-Ebeid et al. .... 382/128 |
| 2006/0149129 | A1 | * | 7/2006  | Watts et al. .................. 600/113 |
| 2007/0109299 | A1 |   | 5/2007  | Peterson                              |
| 2007/0161885 | A1 | * | 7/2007  | Kimchy ....................... 600/407 |
| 2007/0276214 | A1 | * | 11/2007 | Dachille et al. .............. 600/407 |

OTHER PUBLICATIONS

"bowel." The American Heritage® Dictionary of the English Language, Fourth Edition. Houghton Mifflin Company, 2004. Answers. com Aug. 10, 2009. http://www.answers.com/topic/bowel.*

* cited by examiner

*Primary Examiner* — Brian Casler
*Assistant Examiner* — Joseph M Santos
(74) *Attorney, Agent, or Firm* — Schwegman, Lundberg & Woessner, P.A.

(57) ABSTRACT

A method of operating on volumetric imaging data representing organ anatomy includes determining whether a polyp location within a specified range from a viewing point is visible, or hidden by an anatomical feature, and marking the polyp as visible or hidden with a viewable indicator.

21 Claims, 14 Drawing Sheets

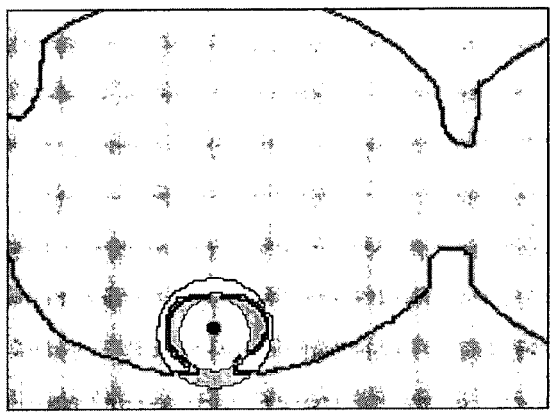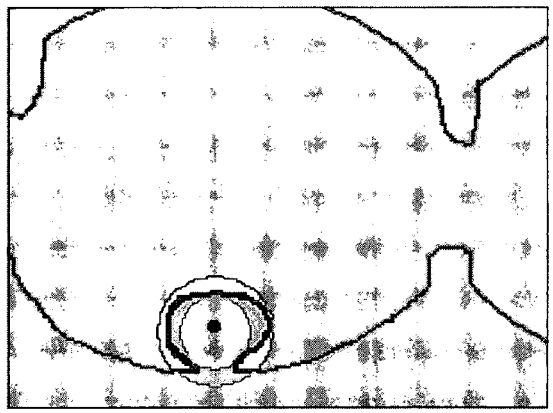
FIG. 15A  FIG. 15B
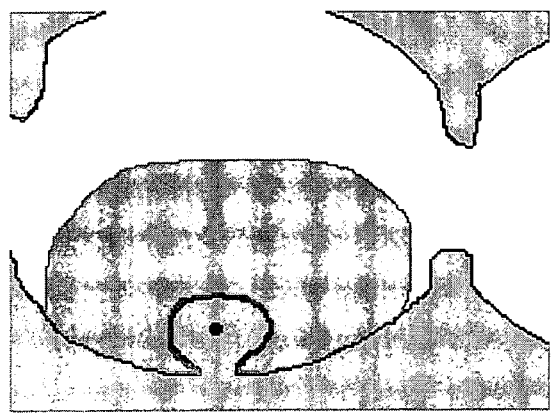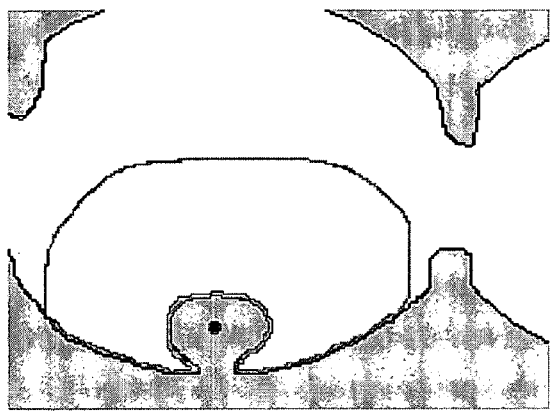
FIG. 16A  FIG. 16B

SYSTEMS AND METHODS FOR VIRTUAL IDENTIFICATION OF POLYPS

RELATED APPLICATION

This application claims the benefit of U.S. Provisional Application Ser. No. 60/687,638, filed Jun. 2, 2005 under 35 U.S.C. §119(e).

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever. The following notice applies to the software and data as described below and in the drawings that form a part of this document: Copyright 2005, Vital Images, Inc, all rights reserved.

TECHNICAL FIELD

This patent document pertains generally to presentation of virtual images of anatomy, and more particularly, but not by way of limitation, to systems and methods for virtual identification of polyps.

BRIEF DESCRIPTION OF THE FIGURES

Embodiments of the present invention are illustrated by way of example and not limitation in the FIG.s of the accompanying drawings in which:

FIG. 15A is a schematic of a highlighted cluster, and FIG. 15B is a schematic of an approximated polyp surface, according to an example embodiment.

FIG. 16A is a schematic of a ambient cloud, and FIG. 16B is a schematic of an ambient cloud boundary, according to an example embodiment.

DETAILED DESCRIPTION

A virtual colonoscopy uses volumetric imaging data to provide a rendered view of an interior of the colon so that polyps can be non-invasively detected and viewed by a physician. The colon is emptied, cleansed, and air is typically introduced. An external computed tomography (CT), magnetic resonance imaging (MRI) or other imaging device is used to obtain volumetric data of the colon. The volumetric data is then processed to identify the imaged structure associated with the colon or other organ of interest.

In one example, a rendered three-dimensional (3D) flythrough image is presented to the physician. The flythrough image simulates travel through the 3D colon structure and allows the physician to view any polyps as they pass. However, the interior of the colon is not smooth. Instead, haustral folds protrude from the internal colon walls. Moreover, the virtual colon flythrough is typically presented from an imaginary single viewing point having a limited (typically conical) field-of-view, which is sometimes referred to as a viewing frustum. A wider field-of-view allows the physician to see more objects of interest, such as polyps. However, the wider field-of-view also increases visual distortion of such objects. Because of the limited field-of-view, and the protruding haustral folds, polyps located behind haustral folds may not be viewable, or may be obscured to the point where they are not noticeable by the diagnosing physician. Therefore, it is desirable to flag or otherwise call attention to such hidden polyps for the viewing physician.

Figure 1:
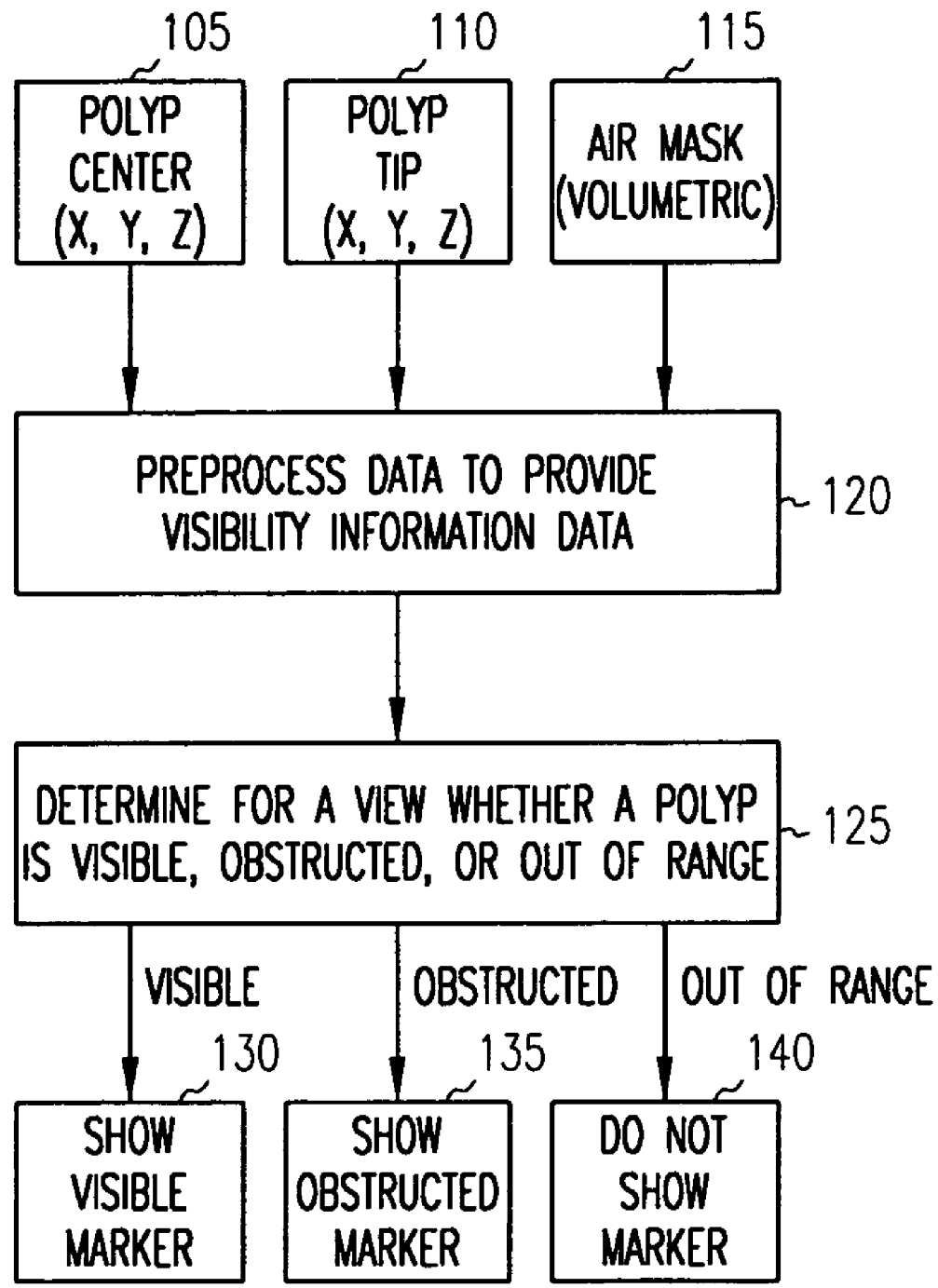
FIG. 1 is a schematic illustration of a method of identifying polyps in a virtual image of an anatomical environment such as the colon, according to an example embodiment.

FIG. 1 is a schematic illustration of a method of identifying polyps in a virtual image of an anatomical environment such as the colon. Data including a polyp center location 105, polyp tip location 110, and air mask 115 are provided as input. The air mask defines an interior of an anatomical region, such as the colon when it is filled with air. The polyp center location 105 and polyp tip location 110 are typically provided as three-dimensional coordinates (e.g. x, y, z). At 120, the data is preprocessed provided visibility information about a polyp and its relation to virtual anatomy in the vicinity of the polyp. In an example, a polyp display manager manages polyp visibility information. At 125, it is determined whether one or more polyps is visible, obstructed, or out of range for a particular virtual vantage point.

Figure 2A:
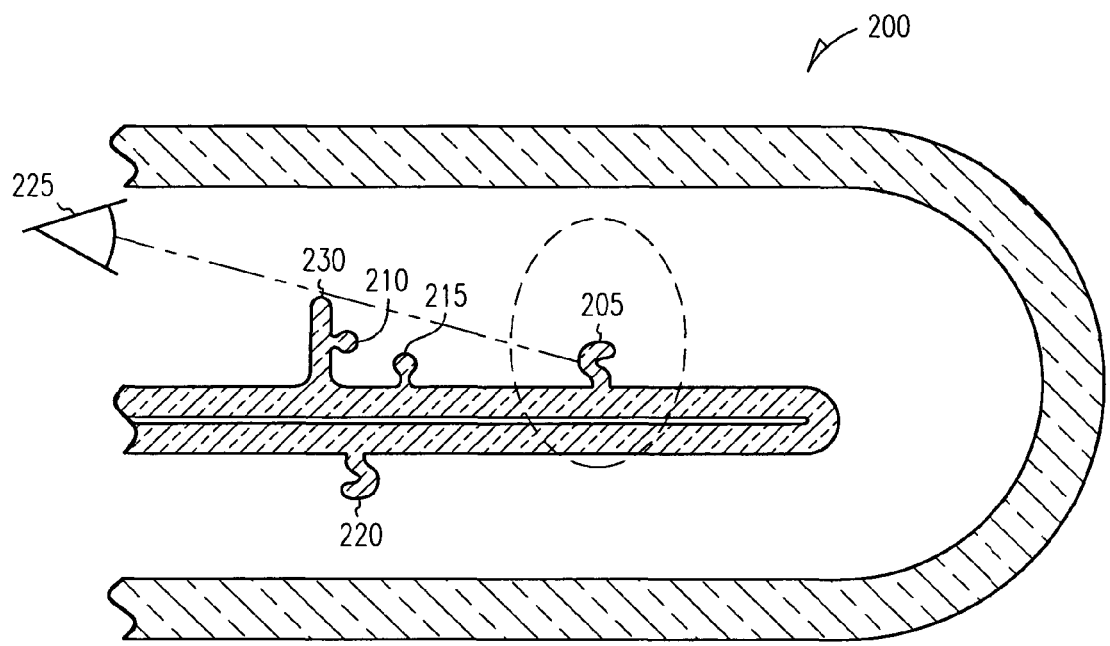
FIG. 2A shows a section of a colon, four polyps, and a vantage point within the section of colon used in rendering an image, according to an example embodiment.

FIG. 2A shows a section of a colon 200 and four polyps 205, 210, 215, and 220. The section of the colon 200 shown in FIG. 2A is essentially U-shaped. A virtual vantage point 225 is shown in FIG. 2A. Polyp 205 is visible from the vantage point 225 shown in the figure. Polyps 210 and 215 are obstructed by a haustral fold 230 in the colon. Polyp 220 is around a bend in the colon and is considered out of range even though it is closer to the vantage point 225 than visible polyp 205. Two sidewalls of the colon 200 are positioned between the polyp 220 and the vantage point 225.

Returning to FIG. 1, if a polyp is determined at 125 to be visible, the polyp is identified as a visible polyp, for example using a marker such as a triangle. The marker is preferably substantially smaller than a typical polyp so as to avoid excessively obscuring virtual anatomy on or around the polyp. If a polyp is determined to be obstructed, the obstructed polyp is identified as such, for example using a different marker such as a square. In an example, the square is projected on the sight line between the center of the polyp and the virtual vantage point and overlayed on onto a visible surface of the obstructing anatomical feature.

Figure 2B:
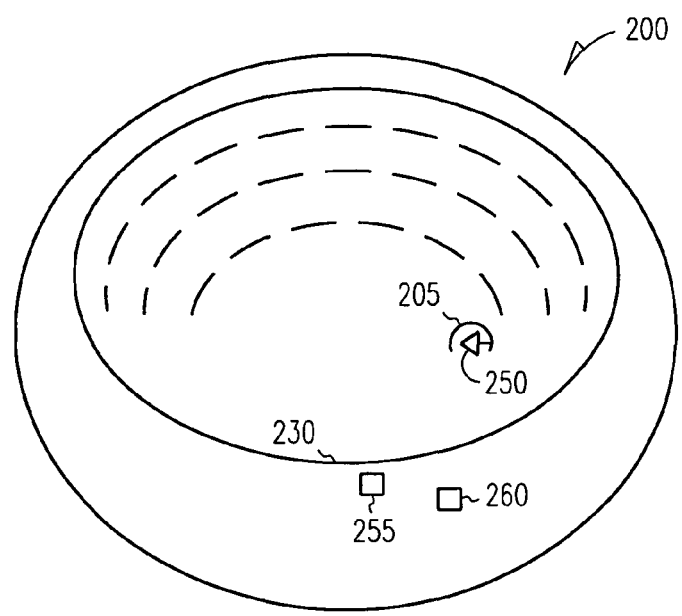
FIG. 2B shows a perspective view of a portion the colon of FIG. 2A with markers as rendered, according to an example embodiment.

FIG. 2B shows a perspective view of a portion the colon 200 of FIG. 2A. Polyp 205 is visible and marked with a triangle 250. Polyps 210 and 215 are obstructed by fold 230, and their location is denoted with squares 255, 260.

Figure 3:
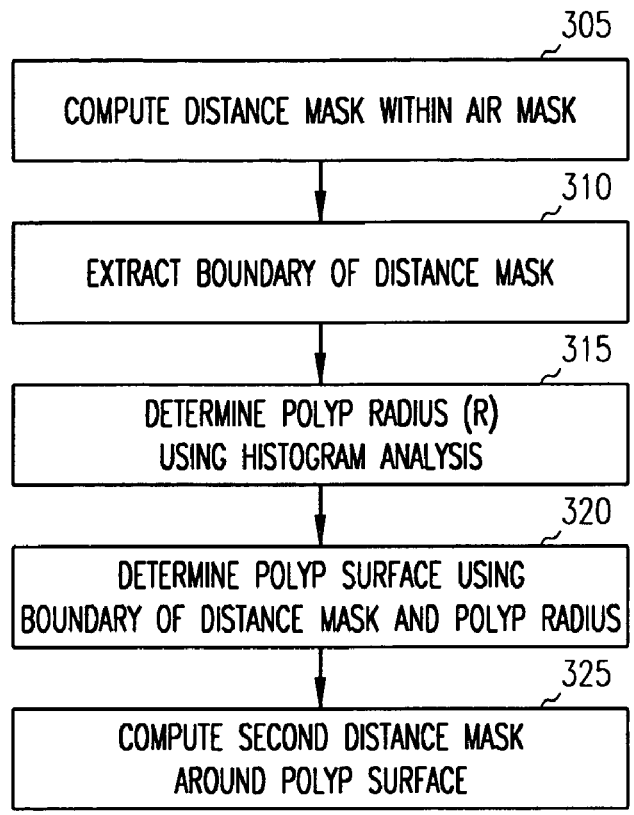
FIG. 3 is a flow diagram that illustrates an example of the preprocessing of data to provide visibility information data, according to an example embodiment.
Figure 4:
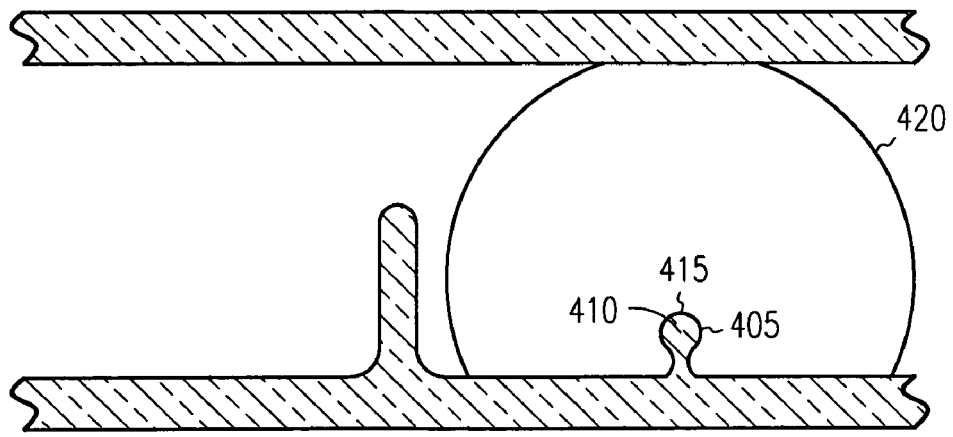
FIG. 4 is a schematic diagram showing a polyp, a polyp center, a polyp tip, and a distance mask (or cloud), according to an example embodiment.

The flowchart in FIG. 3 schematically illustrates an example of the preprocessing executed at 120 in FIG. 1. At 305, a distance mask within an air mask is computed. The distance mask is at a distance from a polyp. The distance mask includes substantially all of the voxels representing air within a selected geodesic distance. A geodesic distance is a minimum distance along a path which lies completely within the air mask. The colon 200 is filled with air. Therefore, the image of the colon, when broken down into small volumes, is that of either air or tissue. A small volume is referred to as a voxel. Voxel is short for volume pixel. A voxel is a small distinguishable box-shaped part of a three-dimensional image. Voxelization is the process of adding depth to an image using a set of cross-sectional images known as a volumetric dataset. These cross-sectional images (or slices) are made up of pixels. The space between any two pixels in one slice is referred to as interpixel distance, which represents a real-world distance. The distance between any two slices is referred to as interslice distance, which represents a real-world depth. The dataset is processed when slices are stacked in a computer memory based on interpixel and interslice distances to accurately reflect the real-world sampled volume. Additional slices are created and inserted between the dataset's actual slices so that the entire volume is represented as a substantially solid block of data. Once the dataset exists as a substantially solid block of data, the pixels in each slice have taken on volume and are now voxels. The voxels undergo an opacity transformation. Opacity transformation gives a voxel an opacity value. The opacity value of air is different than the opacity value of tissue or flesh (non-air), and more specifically, the opacity value of colon tissue (non-air). For voxels within a specified distance ("Max Distance") of the polyp tip, it is determined whether the voxel is air or non-air (e.g. flesh.) In other words, the voxels within a volumetric sphere that is within a specified distance (the Max Distance) from the polyp tip will be analyzed to determine if the voxel has an opacity value associated with air or an opacity value associated with non-air (tissue or flesh). In an example, the Max Distance is specified as 50 mm. The result of the distance mask operation can be thought of as forming a "cloud" within the air mask (i.e. within the colon.) and determining or assigning values of air or non-air (tissue or flesh) to the voxels within the cloud. FIG. 4 shows a polyp 405, polyp center 410, polyp tip 415, and distance mask (or cloud) 420.

Figure 6:
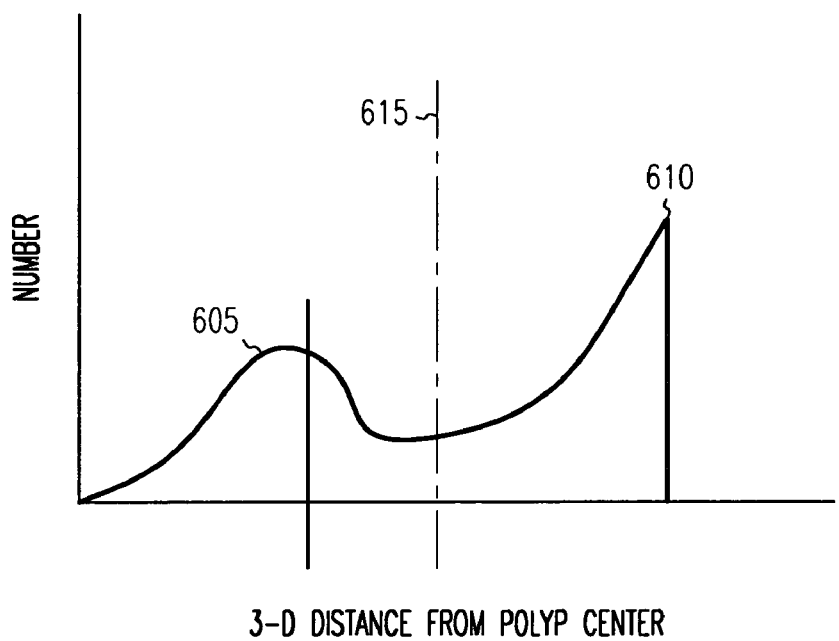
FIG. 6 is histogram of the number of air-tissue interface voxels found in shells at various radii from a particular polyp center, according to an example embodiment.

Returning to FIG. 3, at 310, a boundary is extracted from the distance mask. The boundary is the outer extent of the distance mask, i.e. the voxels of the distance mask that are either at the Max Distance from the polyp tip or are at a transition from air to non-air. At 315, a polyp radius (r) is determined using a histogram analysis. The histogram analysis is schematically illustrated in FIG. 6 and is described below.

Figure 7:
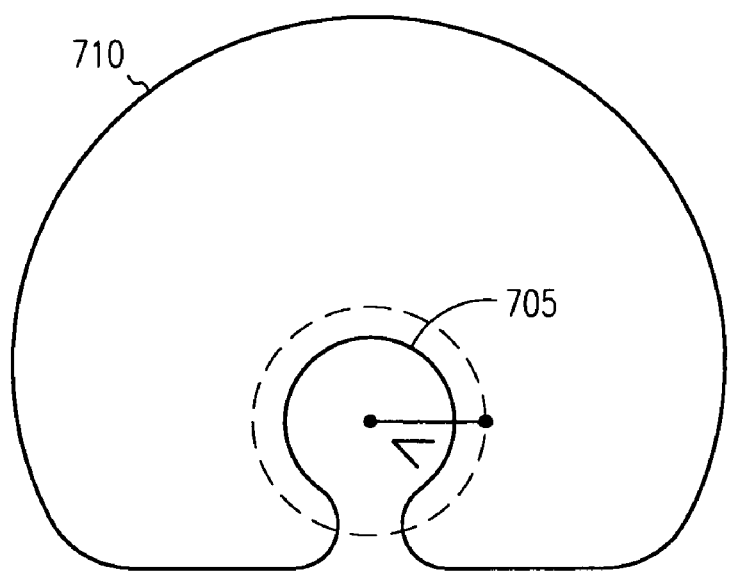
FIG. 7 shows a schematic illustration of the distance mask, and polyp surface, according to an example embodiment.

At 320, the polyp surface is determined using the polyp radius determined at 315 and the boundary of the distance mask. The polyp surface is defined as the voxels of the boundary of the distance mask that are not displaced from the polyp center more than the value (r) determined at 315. In other words, the voxels in the second distance mask that are within (r) of the polyp center make up the polyp surface. FIG. 7 shows a schematic illustration of the distance mask 710 and polyp surface 705.

Figure 8:
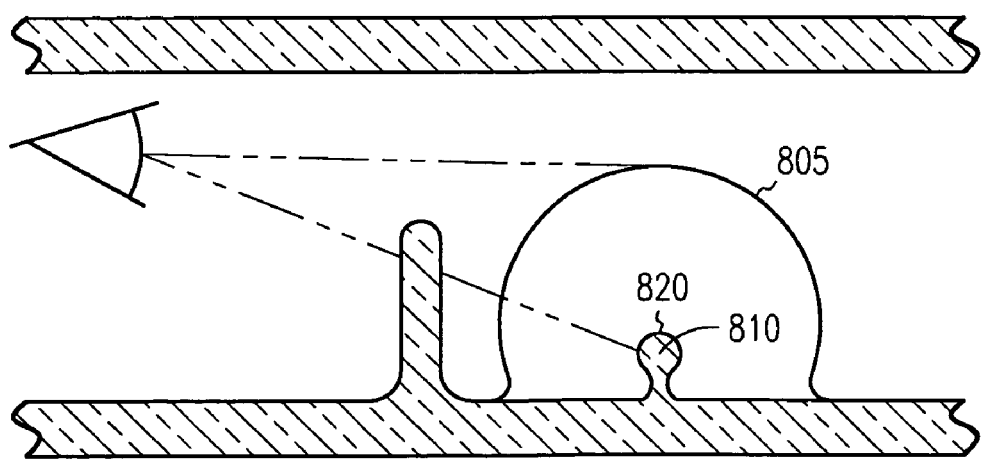
FIG. 8 shows a second distance mask, and a polyp having an outer surface, according to an example embodiment.

Returning again to FIG. 3, at 325, a second distance mask (Max Obstruction Cloud) is computed using the polyp surface determined at 320. The second distance mask includes the universe of voxels that are less than a second geodesic distance (Max Obstruction Cloud Distance) from the polyp center or at a transition between air and non-air. FIG. 8 shows a second distance mask 805 and a polyp 810 having an outer surface 820. The second distance mask 805 is substantially spherically shaped and has a radius less than the first distance mask 420 (shown in FIG. 4).

Figure 5:
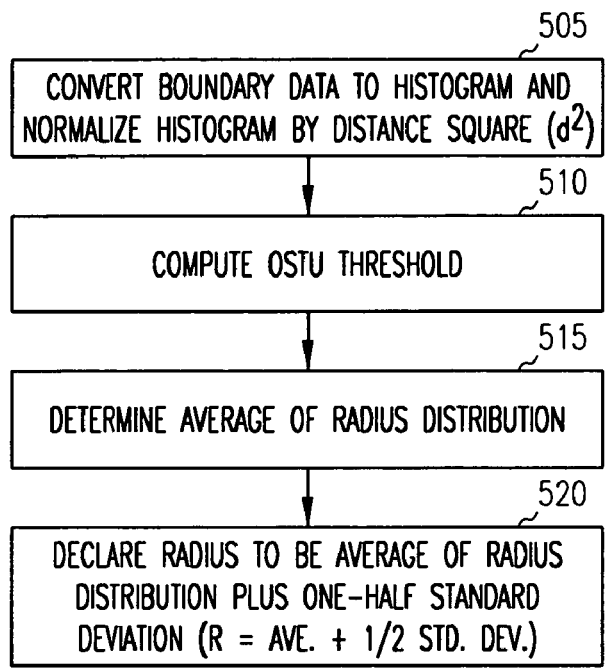
FIG. 5 is a flow diagram for an example histogram analysis, according to an example embodiment.

FIG. 5 shows an example histogram analysis. At 505, the boundary from the distance mask is converted to a histogram and normalized using distance d squared. The data is preferably normalized to account for the fact that the raw data would otherwise over-emphasize points that are farther from the polyp center because the number of voxels increases in proportion to $d^2$, where d is the distance from the polyp center. In other words, at a larger distance, the surface area of the sphere is larger and the number of voxels on the surface of a selected sphere will be larger for larger distances. Finding the surface of the polyp includes counting the distance mask boundary voxels associated with a plurality of spherical shells at various distances from the polyp center 410. At a first selected spherical distance from the polyp center 410 (first shell), the number of voxels residing in the shell and the distance mask boundary are counted. This process is repeated for one or more other selected spherical distances from the polyp tip (shells). These voxel counts are normalized based on the square of the radius of the sphere or on the surface area of the selected sphere at the selected spherical distance and compiled into a histogram. The histogram includes the relative percentages of tissue-air interface voxels for the various selected spherical distances from the polyp tip. The surface of the polyp is found when a first shell has a relative maximum proportion of these boundary voxels.

FIG. 6 shows an example histogram of the number of air-tissue interface voxels found in shells at various radii from a particular polyp center, according to an example embodiment. A first peak 605 corresponds to an approximate radius of the polyp. A second peak 610 corresponds to an outer boundary of the distance mask (or cloud). A polyp is attached to the wall of the colon 200 (see FIG. 2) and at the outer boundary of the distance mask, the number of voxels is normalized to the radius of the sphere will rise since there will be a number of air-tissue voxels associated with the wall of the colon 200 (see FIG. 2) to which the polyp is attached that are counted when the shell or radius is large and incorporates air-tissue voxels from the sidewall of the colon. Thus, the rise at the end of the histogram is not indicative of the surface of the polyp.

Returning to FIG. 5, at 510, an otsu threshold is determined. FIG. 6 shows that the otsu threshold 615 provides a boundary between the first peak 605 corresponding to the approximate radius of the polyp and the second peak 610. Returning again to FIG. 5, at 515, an average of the distribution around the first peak 605 is computed. At 520, the effective radius of the polyp is declared (determined) to be the sum of the average radius determined at 515 and one-half of the standard deviation of the distribution around the first peak 605.

Figure 9:
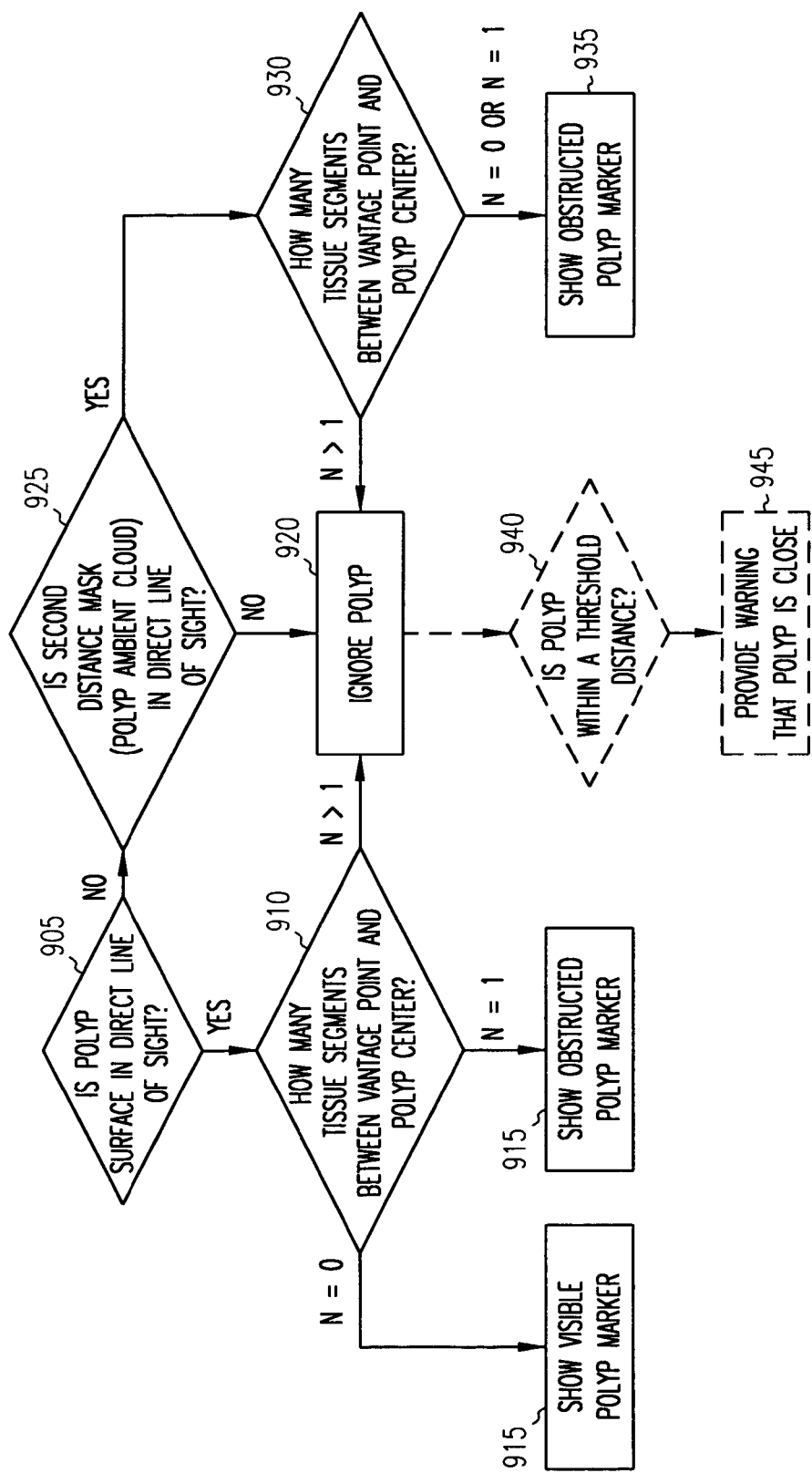
FIG. 9 is a flow diagram illustrating a method for determining whether a polyp surface is within a direct line of sight of a vantage point, according to an example embodiment.

Turning now to FIG. 9, at 905, it is determined whether a polyp surface is within a direct line of sight of a vantage point. In one example, this is determined with a ray-casting operation from a vantage point, such as vantage point 225 (shown in FIG. 2A). If the polyp surface is in the direct line of sight, at 910, it is determined how many tissue segments are between the vantage point and the polyp center. (Note that in one example, operation 905 is determined with reference to the polyp surface and operation 910 is determined with respect to the polyp center.) If there are no tissue segments (n=0) between the vantage point and the polyp center, the marker is indicated as visible (e.g. using a triangle marker). The triangle marker indicates that the polyp will be visible during the virtual fly through. In an example embodiment, only tissue segments that are thicker than a specified threshold thickness are counted in operation 910. For example, a very thin segment may not be tissue and thus may not be shown in a virtual image of the colon.

If there is one tissue segment (n=1) between the vantage point and the polyp center, the polyp is indicated as obstructed (e.g. using a square marker.) This indicates that there is one tissue segment, such as wall, between the polyp and the vantage point. If there is more than one tissue surface between the vantage point and the polyp center, the polyp is ignored and no indicator is shown. This indicates that there are more than one tissue segment, such as two sidewalls, between the vantage point and the polyp. For example, the polyp 220 may be around the corner in a u-shaped section of the colon 200 (see FIG. 2A). This polyp has been passed already or will be coming up in an upcoming section of the colon and therefore will not be marked as within the range of vision at this time during the virtual fly through. Optionally, at 940, it is determined whether the polyp is within a threshold distance of the vantage point, and if it is within the threshold distance, an indication and/or warning is delivered that a polyp is close. This allows a user to anticipate an upcoming polyp in a fly-through or search for polyps in a virtual model, for example. At 925, it is determined whether a second distance mask (polyp obstruction cloud) is visible from the vantage point. If the second distance mask is not visible, the polyp is ignored at 920. If the second distance mask is in the direct line of sight, at 930, it is determined how many tissue segments are between the vantage point and the polyp center. If there are more than one (n>1) tissue segment is between the vantage point and the second distance mask, the polyp is ignored at 920. If (n=0) or one (n=1) tissue segments are between the vantage point and the second distance mask, the polyp is shown indicated to be obstructed, for example using a square marker.

Referring back to FIG. 2A, a ray-casting operation from the vantage point 225 would indicate that polyp 205 is in the direct line of sight, so polyp 205 is indicated in FIG. 2B to be visible. Polyps 210 and 215 are not in a direct line of sight from the vantage point, but their respective masks would be in the direct line of sight, so they would be indicated as obstructed. FIG. 8 for example shows a polyp 810 that is not in a direct line of sight and that has a second distance mask (obstruction cloud) that is in a direct line of sight, so the polyp would be indicated as obstructed. It is understood that traversing the tissue that makes up the polyp itself is not considered a tissue segment when counting the tissue segments between the vantage point and the polyp center. The tissue that makes up the polyp itself will be at the distal end of the line of sight from the vantage point.

Figure 10:
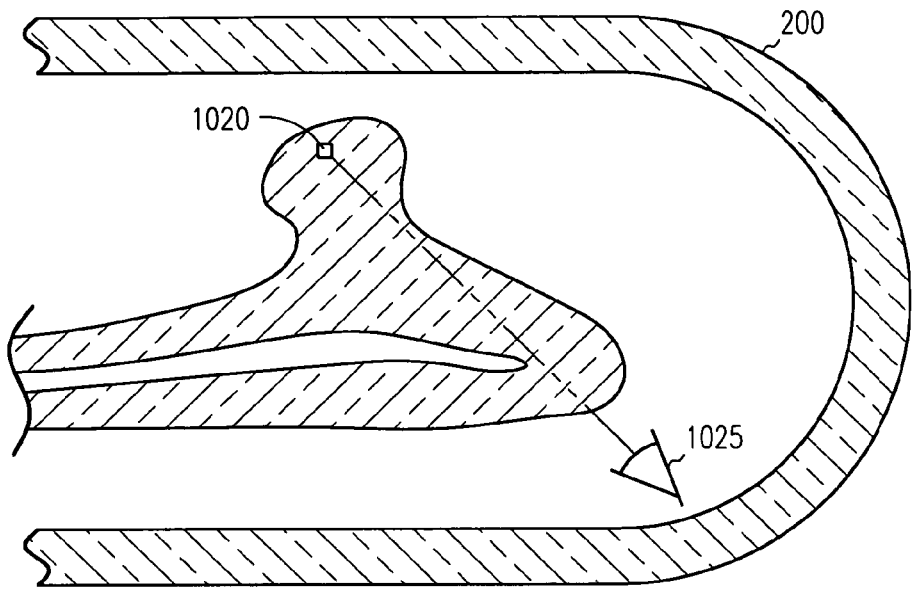
FIG. 10 shows another diagram of a polyp and a vantage point within a section of the colon 200, according to an example embodiment.

FIG. 10 shows another schematic diagram of a polyp and a vantage point within a section of the colon 200. The polyp 1020 is located near a bend in the colon 200. From a selected vantage point 1025, there is only one tissue segment at the distal end of the ray from the vantage point 1025 to the point of the polyp 1020. There is no tissue segments between the distal end tissue and the vantage point 1025 yet the polyp 1025 is around the bend and should be ignored.

Figure 11:
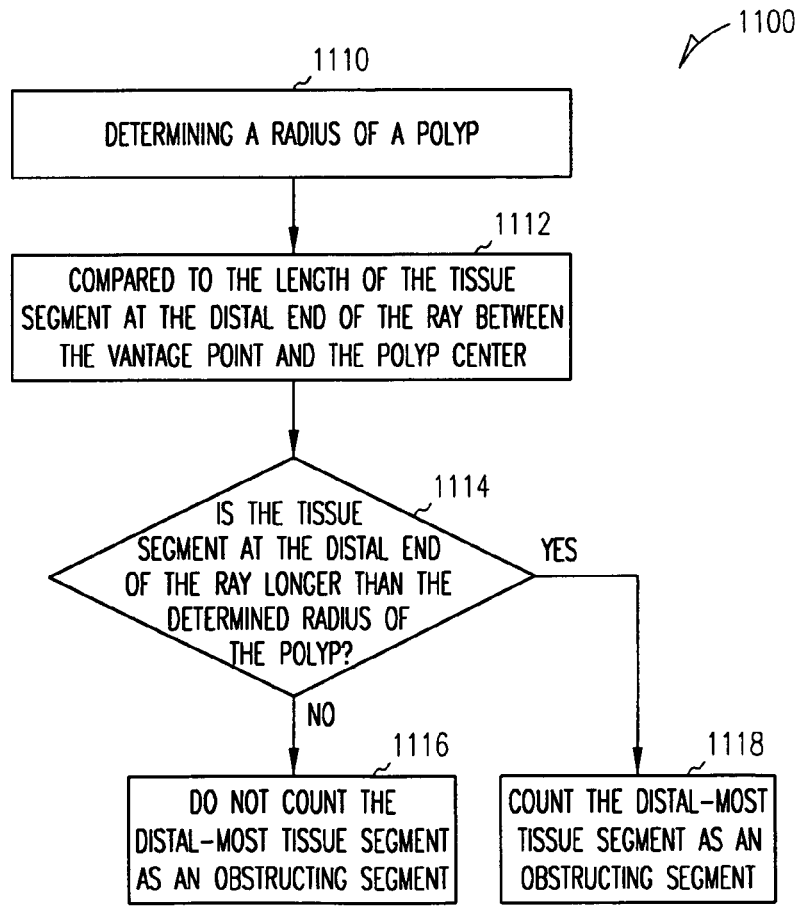
FIG. 11 is a flow diagram of another method for an additional criterion for determining when a polyp is visible or within a direct line of sight of a vantage point, according to an example embodiment.

FIG. 11 is a flow diagram of another method 1100 for an additional criterion for determining when a polyp 1020 is visible or within a direct line of sight of a vantage point 1025, according to an example embodiment. The method 1100 includes determining a radius of a polyp 1110, such as a maximum radius of a polyp. The radius of the polyp is then compared to the length of the tissue segment at the distal end of the ray between the vantage point and the polyp center, as depicted by reference number 1112. Then a decision is made as to whether the tissue segment at the distal end of the ray is larger than the determined radius of the polyp, as depicted by decision box 1114. If the tissue segment at the distal end of the ray is longer than the determined radius of the polyp, then the distal-most tissue segment is counted as an obstructing segment, as depicted by reference number 1116. If the tissue segment at the distal end of the ray is not longer than the determined radius of the polyp, then the distal-most tissue segment is not counted as an obstructing segment, as depicted by reference number 1118. In one example embodiment, this comparison of the length of the last tissue segment along the line-of-sight ray with the polyp's radius is done in addition to the other criteria evaluation for determining visibility/obstruction.

In general, the following conditions must be satisfied before marking a polyp as visible during a rendering of a virtual fly through the colon: At least one voxel on the polyp surface must be directly visible. There also would be no tissue segments of significant size along the line from eye to polyp center, other than the last tissue segment. Furthermore, last tissue segment along the line from eye to polyp center must be approximately equal to the radius of the polyp.

In general, the following conditions must be satisfied before marking a polyp as obstructed or hidden from view during a rendering of a virtual fly through the colon: At least one (or more) of the above visibility criteria is not satisfied, and at least one voxel on the ambient distance mask associated with the polyp is directly visible. Furthermore, one of the following must be satisfied in order to mark the polyp as obstructed or hidden: A. The last tissue segment along the line from eye to polyp center must be approximately equal to the radius of the polyp, and no more than one tissue segment of significant size (not counting the last segment) is along the line from eye to polyp center, or B. The last tissue segment along the line from eye to polyp center is not approximately equal to the radius of the polyp, and there is no tissue segments of significant size along the line from eye to polyp center, other than the last tissue segment.

In an example, the methods illustrated in FIGS. 3, 5, 9 and 11 are performed for a plurality of polyps for a view in a virtual image. In an example, these methods are performed for each polyp. In another example, these methods are performed for a group of polyps that are within a threshold distance of a vantage point and/or meet other criteria. In still another example, the methods are performed by a computer or with the assistance of a computer. One example embodiment includes a computer-assisted method of operating on volumetric imaging data representing organ anatomy. The method includes determining whether a polyp location within a specified range from a viewing point is visible or hidden by an anatomical feature, and providing a viewable indicator of whether the polyp is visible or hidden.

Figure 12:
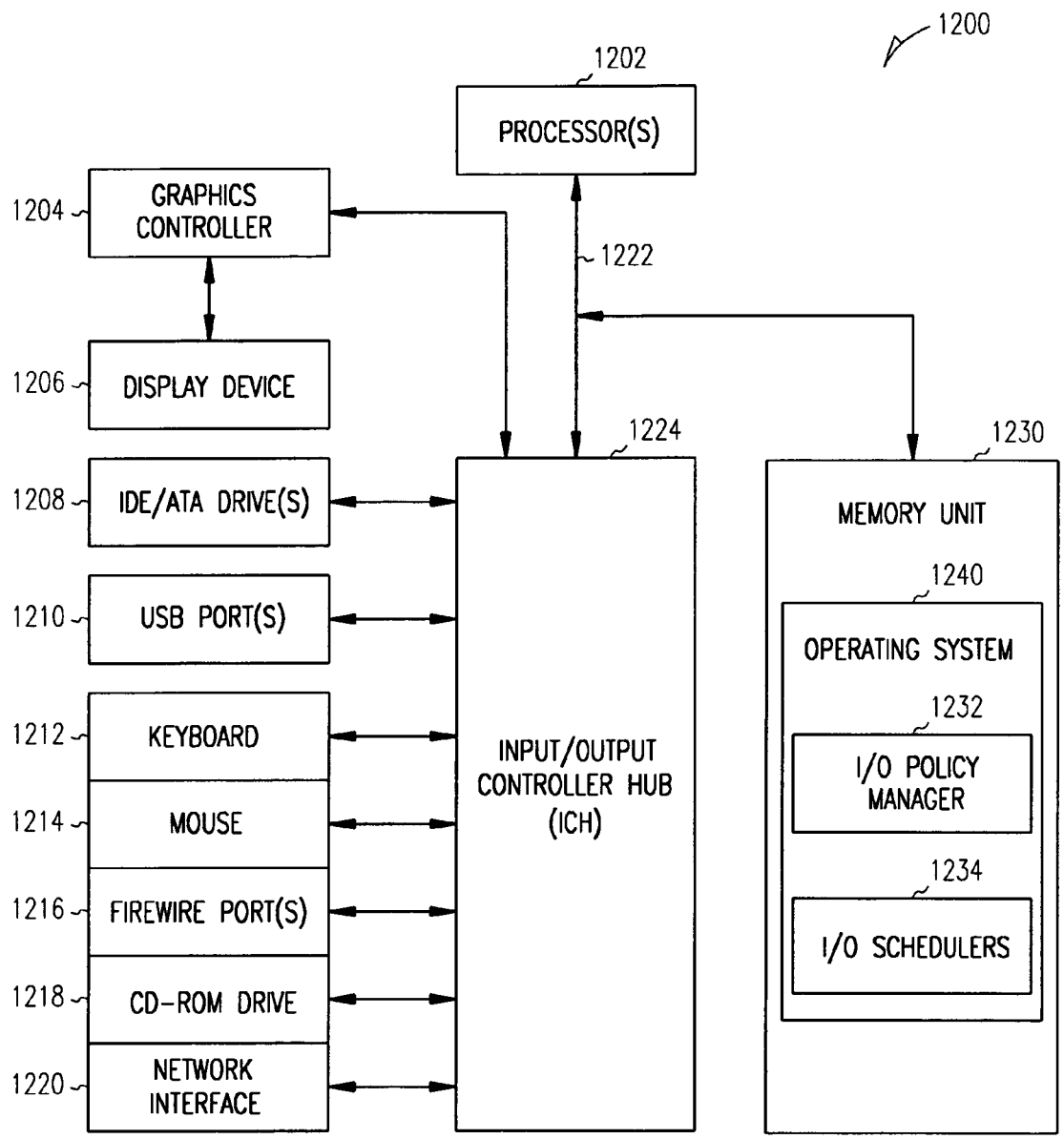
FIG. 12 illustrates an example computer system used in conjunction with certain embodiments.

FIG. 12 illustrates an example computer system used in conjunction with certain embodiments of the invention. As illustrated in FIG. 12, computer system 1200 comprises processor(s) 1202. The computer system 1200 also includes a memory unit 1230, processor bus 1222, and Input/Output controller hub (ICH) 1224. The processor(s) 1202, memory unit 1230, and ICH 1224 are coupled to the processor bus 1222. The processor(s) 1202 may comprise any suitable processor architecture. The computer system 1200 may comprise one, two, three, or more processors, any of which may execute a set of instructions in accordance with embodiments of the present invention.

The memory unit 1230 includes an operating system 1240, which includes an I/O scheduling policy manager 1232 and I/O schedulers 1234. The memory unit 1230 stores data and/or instructions, and may comprise any suitable memory, such as a dynamic random access memory (DRAM), for example. The computer system 1200 also includes IDE drive(s) 1208 and/or other suitable storage devices. A graphics controller 1204 controls the display of information on a display device 1206, according to embodiments of the invention.

The Input/Output controller hub (ICH) 1224 provides an interface to I/O devices or peripheral components for the computer system 1200. The ICH 1224 may comprise any suitable interface controller to provide for any suitable communication link to the processor(s) 1202, memory unit 1230 and/or to any suitable device or component in communication with the ICH 1224. For one embodiment of the invention, the ICH 1224 provides suitable arbitration and buffering for each interface.

For one embodiment of the invention, the ICH 1224 provides an interface to one or more suitable integrated drive electronics (IDE) drives 1208, such as a hard disk drive (HDD) or compact disc read-only memory (CD ROM) drive, or to suitable universal serial bus (USB) devices through one or more USB ports 1210. For one embodiment, the ICH 1224 also provides an interface to a keyboard 1212, a mouse 1214, a CD-ROM drive 1218, and one or more suitable devices through one or more firewire ports 1216. The ICH 1224 also provides a network interface 1220 though which the computer system 1200 can communicate with other computers and/or devices.

In one embodiment, the computer system 1200 includes a machine-readable medium that stores a set of instructions (e.g., software) embodying any one, or all, of the methodologies for dynamically loading object modules described herein. Furthermore, software can reside, completely or at least partially, within memory unit 1230 and/or within the processor(s) 1202.

In one example embodiment, the computer or information handling system 1200 stores information used for computing the location and visibility of polyps and then renders a view from a given eye/frustum position. The PolypDisplayInfo class stores the information used for computations. The PolypDisplayManager computes the visibility states and the views for each rendering of an image. Given voxel positions of the center of a polyp and a tip point near the surface, the PolypDisplayInfo class stores three basic structures for computing visibility within the colon air mask. First, the polyp's surface is approximated and stored as a list of voxels at the tissue/air interface of the polyp. Second, an ambient air mask is computed at some prescribed geodesic distance away from the polyp's surface and the boundary of this mask is stored as a list of voxels. Finally, a proximity mask consisting of all voxels within some prescribed proximity of the polyp is computed and stored as a volume mask.

At each render, visibility states, from a given eye/frustum, are computed by the PolypDisplayManager class using the above polyp information (in flythrough mode) or view vector/bounding box (in biopsy mode).

The PolypDisplayInfo object stores the approximate polyp surface, ambient cloud boundary, and proximity mask, given its centroid, a tip point near the air interface, and an abdominal air mask. The polyp surface is only an approximation, and thus so are the subsequently computed data.

Figures 13A, 13B, 13C:
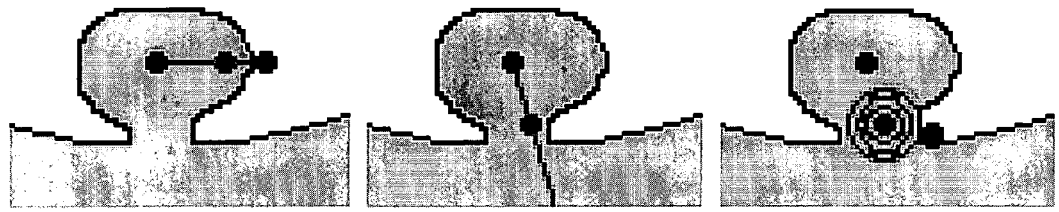
FIGS. 13A, 13B and 13C show several steps in locating a single seed point at the polyp-air interface, according to an example embodiment.

FIGS. 13A, 13B and 13C show several steps in locating a single seed point at the polyp-air interface. To generate the data for the PolypDisplayInfo object, the first step is to find a single seed point at the polyp-air interface. This is done by searching along the ray from the centroid point to the tip point until a voxel that is within the air mask (FIG. 13A) is found or until a selected search length threshold (FIG. 13B) is exceeded. In the case where the threshold is exceeded, a second attempt at finding an interface point is made by locating the point on the air mask boundary that is nearest to the given polyp tip point (FIG. 13C). In either case, if the located seed is more than a prescribed distance from the polyp center, the polyp surface approximation (and thus PolypDisplayInfo object creation) fails. The status of the polyp is classified as "invalid" and "inactive".

Figures 14A, 14B:
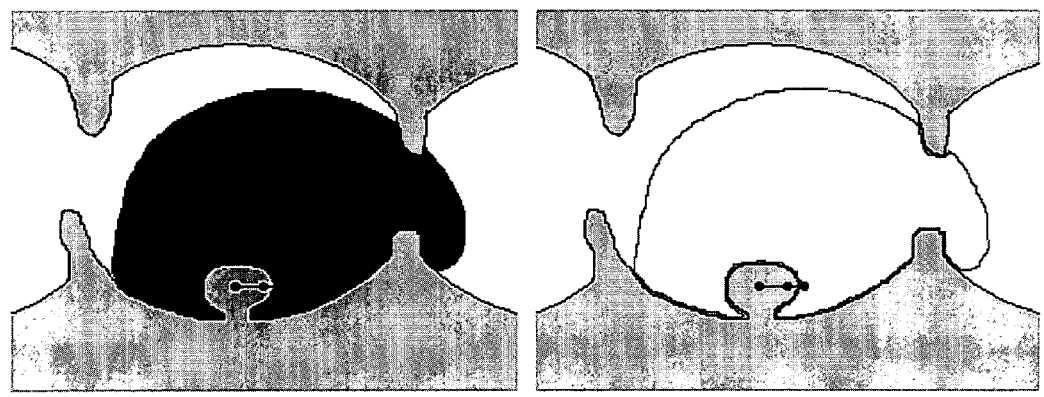
FIG. 14A is an illustration of an initial region of interest as determined from the surface seed.
FIG. 14B is an illustration of a superset of a polyp surface, according to an example embodiment.
Figure 17A:
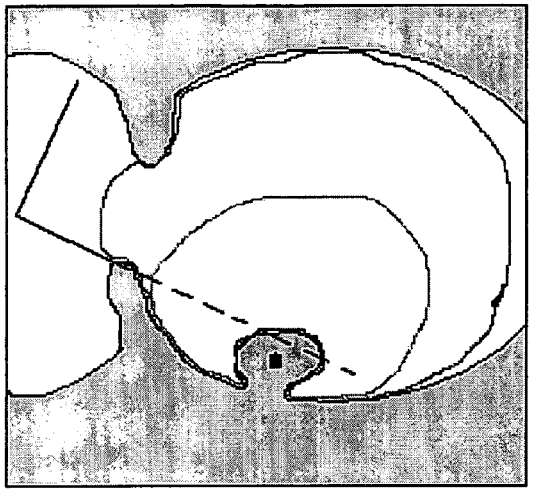
FIGS. 17A-17J illustrate various tests involved in computing the visibility state of a given polyp from a given eye position and a view frustum, according to an example embodiment.
Figure 17B:
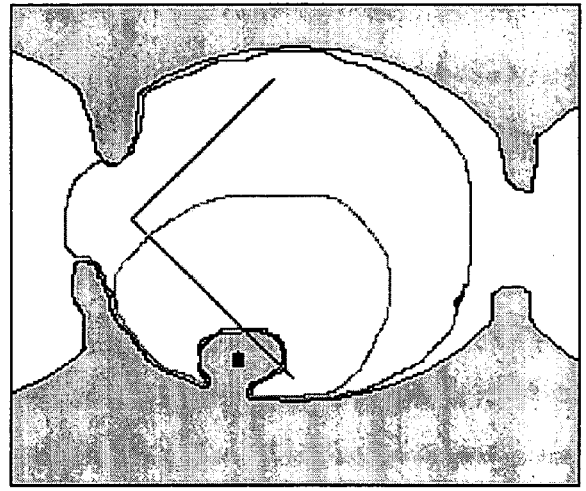
Figure 17C:
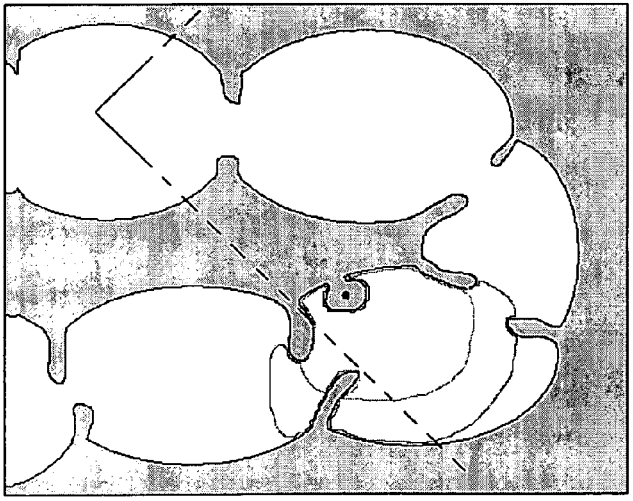
Figure 17D:
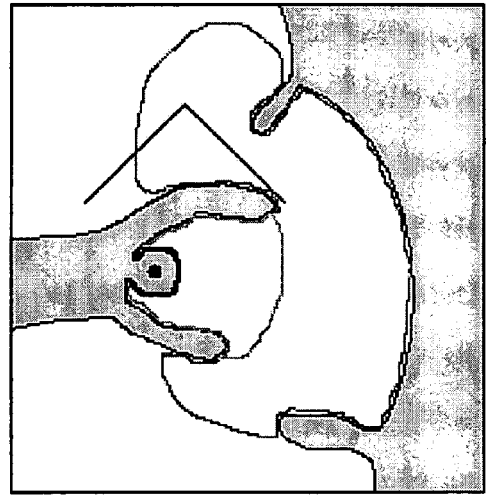
Figure 17E:
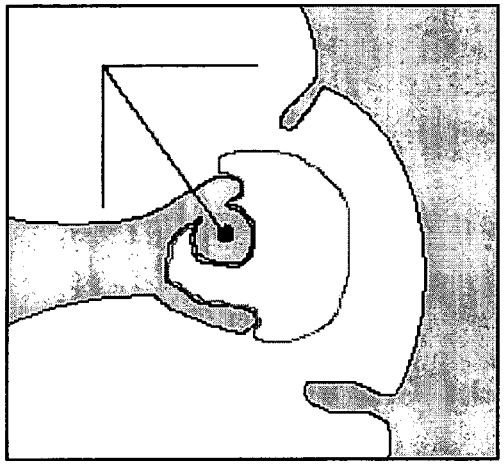
Figure 17F:
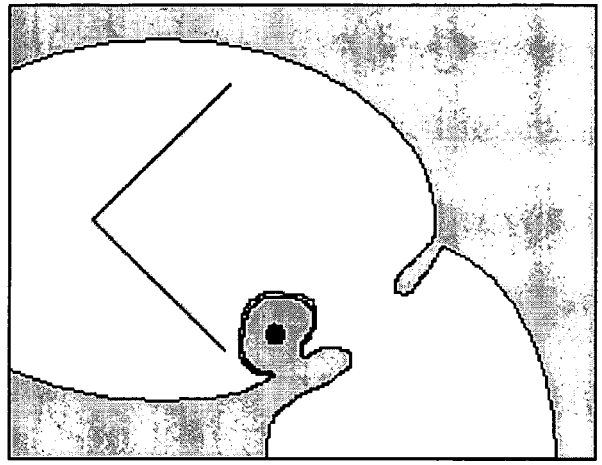
Figure 17G:
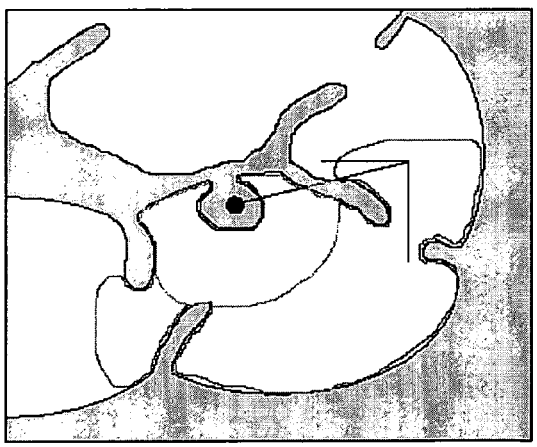
Figure 17H:
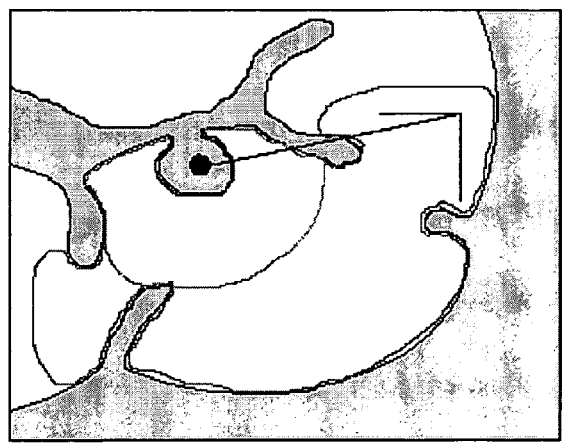
Figure 17I:
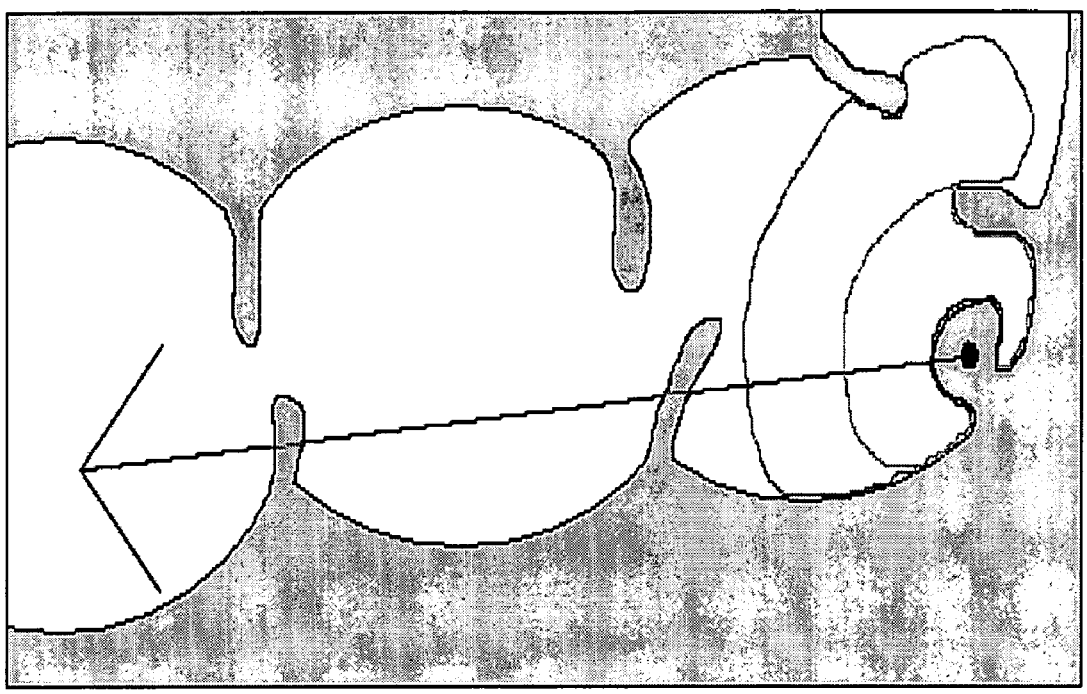
Figure 17J:
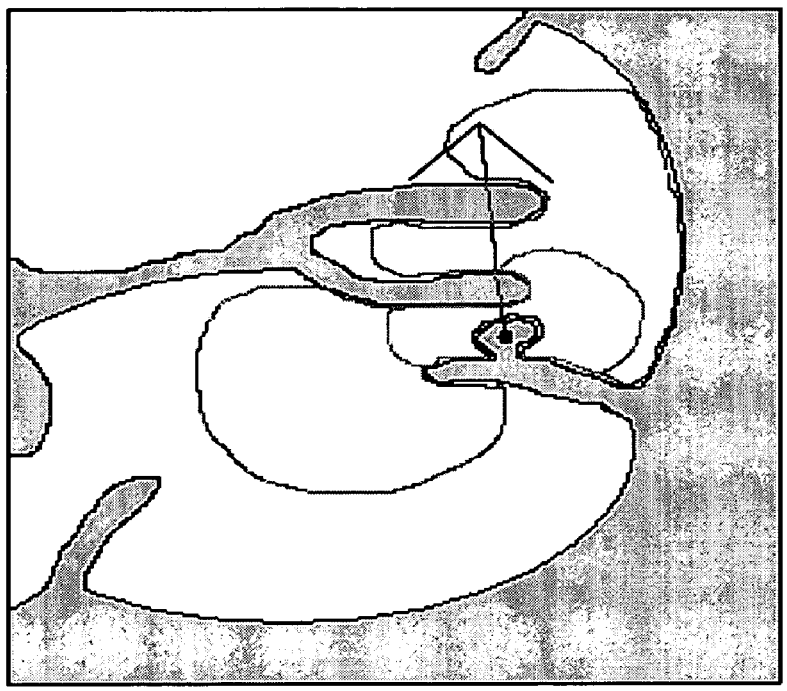

FIG. 14A is an illustration of an initial region of interest as determined from the surface seed, and FIG. 14B is an illustration of a superset of a polyp surface, according to an example embodiment. Now referring to both FIGS. 14A and 14B, once an initial interface seed is found, a region of interest ("ROI") is computed around the polyp by computing the geodesic distance map with an ROI distance>=(proximity dist, ambient dist) within the air mask of all points within an adequately sized bounding box around the surface seed point (see FIG. 2a/14A). This ROI contains all air mask points that are within the ROI distance (computed geodesically) from the surface seed point. The boundary of this ROI is extracted, which includes all voxels at the geodesic distance border, as well as those nearer to the seed point, but at the air-tissue interface. In other words, the boundary is expected to be a super-set of the actual polyp surface (see FIG. 14B).

FIG. 15A is a schematic of a highlighted cluster, and FIG. 15B is a schematic of an approximated polyp surface, according to an example embodiment. Referring to both FIGS. 15A and 15B, the set of true polyp-surface points is expected to constitute an unusually high cluster of points at a particular distance from the polyp's centroid (i.e. the approximate polyp radius) as shown FIG. 15A. This radius is extracted by analyzing the histogram (see FIG. 6) computed over the various distances to the polyp centroid and normalized by the square of the distance to avoid penalizing small radii (which will naturally have less representation due to the discrete nature of the data). The final polyp surface is extracted as the subset of the ROI boundary points whose distance from the polyp centroid is within a tolerance of the approximated polyp radius, as shown in FIG. 15B.

FIG. 16A is a schematic of a ambient cloud, and FIG. 16B is a schematic of an ambient cloud boundary, according to an example embodiment. Referring to both FIGS. 16A and 16B, after the polyp's surface has been approximated, and ambient ROI is generated by computing the geodesic distance map (measured to the polyp surface) of air voxels with maximum geodesic distance given by ambient distance (see FIG. 16A). The boundary of this ROI constitutes the set of ambient cloud surface voxels, which will be used later to determine whether a polyp might be slightly obstructed from the user's line of sight (see FIG. 16B).

The steps involved in computing the visibility state of a given polyp from a given eye position and a view frustum will now be discussed and illustrated with FIGS. 17A-17J. There are three possible states for each polyp: PolypVisible—the polyp's center and some part of its surface are in the direct line of sight, PolypObstructed—part of the polyp's ambient cloud is in the direct line of sight and the polyp's center is obscured by at most one proper tissue segment (e.g. a Haustral fold), and PolypProximal—neither of the above are true, but the eye is within the polyp's proximal cloud.

The visibility classification is dependent on a set of five tests described below. In a set of instructions, sometimes referred to as computer code, executable by a computer 1200 (see FIG. 12), the tests are performed in an order determined by both the speed at which the test can be executed as well as the elimination power of the test itself. In one embodiment, the order in which the tests are applied is reflected in the list below:

Polyp center in view frustum: Very fast. False response eliminates all visibility states except for PolypProximal.
  Number of proper tissue segments between eye and polyp center: Very fast. Response >0 eliminates PolypVisible and response >1 eliminates PolypObstructed. Note that since the polyp centers are typically embedded in the tissue (rather than air), we do not count the last ray entrance into tissue unless the entry point is more than the polyp radius away from the polyp center.
  Surface voxel in the direct line of sight: Fast. Response determines PolypVisible.
  Ambient voxel in the direct line of sight: Slow. Response determines Polyp Obstructed.
  Eye in polyp's proximal cloud: Very fast. False response eliminates PolypProximal.

Of course, the above tests could be applied in a different order in different embodiments of the invention. A visibility state table is shown below (see illustrations below for examples).

Figure 18:
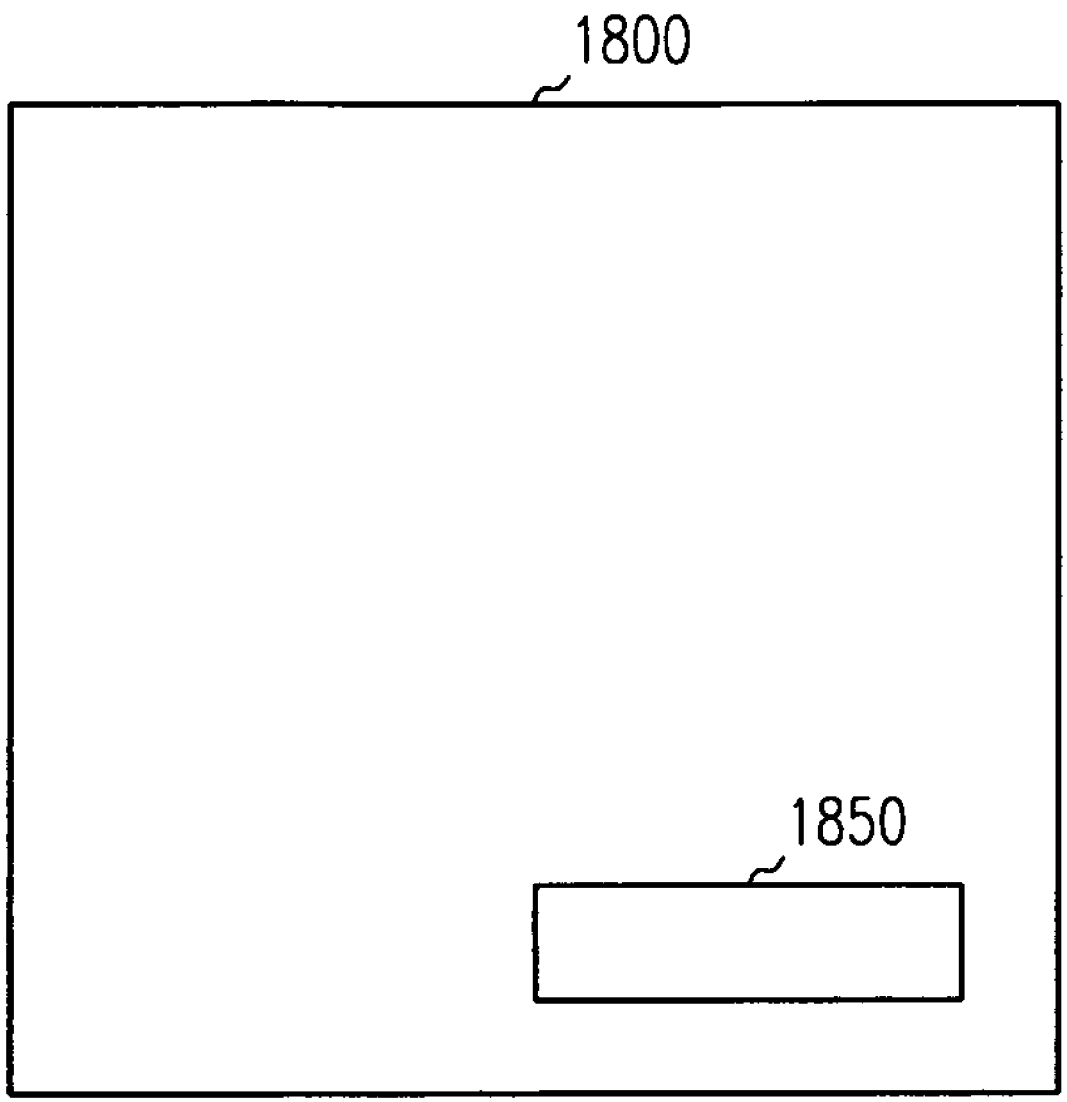
FIG. 18 is a schematic diagram showing a computer readable media having a set of instructions executable by a suitable machine, such as an information handling system or a computer, according to an example embodiment.

FIG. 18 is a schematic diagram showing a computer readable media having a set of instructions executable by a suitable machine, such as an information handling system or a computer, according to an example embodiment. The machine readable medium 1800 includes any type of medium such as a link to the internet or other network, or a disk drive or a solid state memory device, or the like. A machine-readable medium 1300 includes instructions within an instruction set 1850. The instructions, when executed by a machine such as an information handling system or a processor, cause the machine to perform operations that include the methods, such as the ones discussed in FIGS. 3, 5, 9, 11 and 13A-17J.

The indication of polyps as visible or obstructed facilitates analysis and diagnosis of polyps or other features in a virtual colonoscopy or other virtual examination. Visible polyps are locatable and identifiable. Hidden polyps that are obstructed by virtual anatomical features such as a fold of tissue are locatable and identifiable as hidden, thereby prompting a user to adjust the virtual image to show the hidden polyp.

In an alternative, a biopsy view is provided. The biopsy view shows a solid volume that is a subset of the available anatomy. In an example, the biopsy view shows a cube of anatomy of interest, such as anatomy in the vicinity of a polyp. In an example, the biopsy view is orthographic projection rather than a perspective view. An orthographic projection projects lines onto a view plane, as opposed to projecting lines from a single vantage point. The methods described herein can be used with an orthographic biopsy view, with the adjustment that the operations illustrated in FIG. 9 (e.g. operations 905, 910, 925, 930) are determined using parallel ray casting from a vantage plane rather than perspective ray casting using a vantage point.

In an example, visible and obstructed indicators such as square or triangle markers are applied as an overlay onto a virtual image.

The above specification, examples and data provide a complete description of the manufacture and use of the composition of the invention. Since many embodiments of the invention can be made without departing from the scope of the invention, the invention resides in the claims hereinafter appended.

What is claimed is:

1. A computer implemented method of operating on volumetric imaging data representing organ anatomy for virtual identification of polyps, the computer implemented method comprising:

| Polyp center in view frust | Nbr of tissue segs between eye and polyp center | Polyp surf point in direct LOS through air mask | Polyp ambient cloud point in direct LOS through air mask | Eye point in polyp's proximity cloud | Visibility State | FIG. |
|---|---|---|---|---|---|---|
| F | Any | T/F | T/F | F | N/A | 5A |
| F | Any | T/F | T/F | T | Proximal | 5B |
| T | Any | F | F | F | N/A | 5C |
| T | Any | F | F | T | Proximal | 5D |
| T | 0 | F | T | T/F | Obstructed | 5E |
| T | 0 | T | T/F | T/F | Visible | 5F |
| T | 1 | T/F | F | F | N/A | 5C |
| T | 1 | T/F | F | T | Proximal | 5G |
| T | 1 | T/F | T | T/F | Obstructed | 5H |
| T | >1 | T/F | T/F | F | N/A | 5I |
| T | >1 | T/F | T/F | T | Proximal | 5J | receiving the volumetric imaging data into a computing device communicatively coupled to a display;

presenting a three-dimensional (3-D) image of the organ anatomy on the display using the volumetric imaging data, wherein the 3-D image is presented from a variable virtual viewing point within the 3-D image, the variable virtual viewing point being a location within the 3-D image at a specific time, wherein the location of the variable virtual viewing point within the 3-D image is changeable within the 3-D image;

identifying, with the device, a polyp location and generating a distance mask surrounding the polyp location in the volumetric imaging data;

determining, with the device, whether the polyp location is in a direct line of sight of the variable virtual viewing point, or whether the polyp location is hidden from the direct line of sight of the variable virtual viewing point by an intervening anatomical feature but the distance mask surrounding the polyp location is in the direct line of sight of the variable virtual viewing point, as the location of the variable virtual viewing point is changed; and providing a viewable indicator of the polyp location in the 3-D image on the display, wherein the viewable indicator is presented from a viewing perspective of the variable virtual viewing point, the viewable indicator in the direct line of sight of the variable virtual viewing point to indicate a location in the 3-D image at which a polyp at the polyp location is hidden due to the intervening anatomical feature between the polyp and the location of the variable virtual viewing point within the 3-D image.

2. The method of claim 1 wherein determining whether a polyp location is in a direct line of sight of the variable virtual viewing point, or whether the polyp location is hidden from the direct line of sight of the variable virtual viewing point by an intervening anatomical feature, includes determining a number of non-air segments along a ray between the viewing point and a center of the polyp.

3. The method of claim 2 wherein a non-air segment at the end of the ray near the center of the polyp is ignored.

4. The method of claim 2 wherein a non-air segment at the end of the ray near the center of the polyp is ignored when a length of the non-air segment is more than a selected distance, the selected distance being greater than an approximate radius of the polyp.

5. The method of claim 3 wherein the polyp is marked as hidden in the direct line of sight of the variable viewing point when one non-air segment is along the ray between the viewing point and the center of the polyp.

6. The method of claim 3 wherein the polyp is marked as in the direct line of sight of the variable viewing point when no non-air segment is along the ray between the viewing point and the center of the polyp.

7. The method of claim 3 wherein the polyp is unmarked when more than one non-air segment is along the ray between the viewing point and the center of the polyp.

8. The method of claim 1 wherein determining whether a polyp location is in a direct line of sight of the variable virtual viewing point, or whether the polyp location is hidden from the direct line of sight of the variable virtual viewing point by an intervening anatomical feature, includes:

determining a length of a non-air segment between the viewing point and a center of the polyp;

selecting a maximum radius of the polyp; and comparing the determined length of a non-air segment between the viewing point and the center of the polyp to the maximum radius of the polyp.

9. The method of claim 8 further comprising leaving the polyp unmarked when the length of the non-air segment is more than the selected maximum radius of the polyp.

10. The method of claim 1 wherein determining whether a polyp location is in a direct line of sight of the variable virtual viewing point, or whether the polyp location is hidden from the direct line of sight of the variable virtual viewing point by an intervening anatomical feature, includes determining the visibility of the surface of the polyp, the surface of the polyp being generated from another distance mask at the polyp location.

11. The method of claim 1 wherein determining whether a polyp location is in a direct line of sight of the variable virtual viewing point, or whether the polyp location is hidden from the direct line of sight of the variable virtual viewing point by an intervening anatomical feature, further includes determining the visibility of a voxel cloud generated at a selected distance in the air surrounding the surface of the polyp at the polyp location, the surface of the polyp being generated from another distance mask at the polyp location.

12. The method of claim 1 wherein determining whether a polyp location is in a direct line of sight of the variable virtual viewing point, or whether the polyp location is hidden from the direct line of sight of the variable virtual viewing point by an intervening anatomical feature, includes:

determining the visibility of the surface of the polyp at the polyp location, the surface of the polyp being generated from another distance mask at the polyp location; and determining the visibility of a voxel cloud generated at a selected distance in the air surrounding the surface of the polyp at the polyp location.

13. A computer implemented method of operating on volumetric imaging data representing organ anatomy for virtual identification of polyps, the computer implemented method comprising:

receiving the volumetric imaging data into a computing device;

presenting a three-dimensional (3-D) image of the organ anatomy on a display using the volumetric imaging data, wherein the 3-D image is presented from a variable virtual viewing point;

determining and generating, with the device, a first distance mask from a polyp center;

determining, with the device, a radius of the polyp;

determining, with the device, a polyp surface using the polyp radius and the first distance mask;

determining whether the polyp is in a direct line of sight of the variable virtual viewing point, or whether the polyp is hidden from the direct line of sight of the variable virtual viewing point by an intervening anatomical feature of the organ but a second distance mask, further generated, surrounding the polyp is in the direct line of sight of the variable virtual viewing point, using the determined polyp surface as the location of the polyp within the 3-D image, as a location of the variable virtual viewing point within the 3-D image is changed; and marking the polyp location in the 3-D image on the display with a first viewable indicator when the second distance mask surrounding the polyp is in the direct line of sight of the variable virtual viewing point but the polyp is hidden from the direct line of sight of the variable virtual viewing point by the intervening anatomical feature as the variable virtual viewing point is changed, and marking the polyp location with a second viewable marker when the polyp location is in a direct line of sight of the variable virtual viewing point as the variable virtual viewing point is changed, wherein the first and second viewable indicators are presented from a viewing perspective of the variable virtual viewing point.

14. The method of claim 13 wherein determining a radius of the polyp includes a histogram analysis.

15. The method of claim 13 further comprising extracting a boundary from the first distance mask.

16. The method of claim 15 wherein extracting a boundary from the first distance mask includes;
determining a plurality of voxels that are at a specified distance from the polyp center; and
determining a plurality of voxels that are at a transition between air and non-air.

17. The method of claim 16 wherein determining a radius of the polyp includes a histogram analysis of the plurality of voxels that are at a specified distance from the polyp center, and the plurality of voxels that are at a transition between air and non-air.

18. A non-transitory computer readable medium including one or more of a disk drive and a solid state memory device, either located local to a computer or remotely connectable to the computer by a link, wherein the computer readable medium includes computer performable instructions to cause the computer to operate on volumetric imaging data representing organ anatomy for virtual identification of polyps including performing operations comprising:
identifying a polyp location and generating a distance mask surrounding the polyp location in the volumetric imaging data;
determining whether the polyp location or the distance mask surrounding the polyp location is in the direct line of sight of a variable virtual viewing point of a 3-D image, or hidden in the direct line of sight of the variable virtual viewing point of the 3-D image by an intervening anatomical feature as a location of the variable virtual viewing point is changed, the variable virtual viewing point being a location within the 3-D image at a specific time; and
marking the polyp location in the 3-D image on a display, in the direct line of sight of the virtual viewing point, as hidden with a first viewable indicator to indicate a location in the 3-D image at which the polyp is hidden in the direct line of sight of the variable virtual viewing point by the intervening anatomical feature but the distance mask surrounding the polyp location is in the direct line of sight of from the variable virtual viewing point, as the variable virtual viewing point is changed in the 3-D image, wherein the first viewable indicator is presented from a viewing perspective of the variable viewing point.

19. The non-transitory computer readable medium of claim 18 wherein the instructions, when executed by a machine, causes the machine to:
mark the polyp location with a second viewable indicator when the polyp location is in a direct line of sight of the variable virtual viewing point as the variable virtual viewing point varies.

20. The non-transitory computer readable medium of claim 18 wherein the instructions, when executed by a machine, causes the machine to produce an audible signal when the polyp location is within a selected distance from a selected vantage point.

21. The method of claim 1, including changing the viewable indicator when the virtual viewing point is changed and the polyp location changes from being in the direct line of sight of the variable virtual viewing point to being hidden in the direct line of sight of the variable virtual viewing point to, or from being hidden in the direct line of sight of the variable virtual viewing point to being in the direct line of sight of the variable virtual viewing point.

* * * * *